United States Patent [19]

Calvani et al.

[11] Patent Number: 5,166,744
[45] Date of Patent: Nov. 24, 1992

[54] METHOD OF MEASURING THE NONLINEAR REFRACTIVE INDEX COEFFICIENT OF A BISTABLE RESONANT CAVITY OPTICAL COMPONENT

[75] Inventors: Riccardo Calvani, Pino Torinese; Renato Caponi, Turin, both of Italy

[73] Assignee: Cselt - Centro Studi E Laboratori Telecomunicazioni S.P.A., Turin, Italy

[21] Appl. No.: 719,311

[22] Filed: Jun. 21, 1991

[30] Foreign Application Priority Data

Jul. 4, 1990 [IT] Italy ................. 67488 A/90

[51] Int. Cl.⁵ ........................................... G01N 21/41
[52] U.S. Cl. ................................................... 356/128
[58] Field of Search ........................ 356/128; 372/8

[56] References Cited

U.S. PATENT DOCUMENTS 5,007,735  4/1991  Calvani et al. ................. 356/128

OTHER PUBLICATIONS

Applied Optics 2219, vol. 25, No. 10 15 May 1986 S. D. Smith.

Electronics Letters 30 Aug. 1990, vol. 26, No. 18 Calvani et al.

D. Milam and M. J. Weber, "Measurement of nonlinear refractive index coefficient . . . ", Journal of Applied Physics, vol. 47, 1976, pp. 2497 through 2501.

Primary Examiner—F. L. Evans
Attorney, Agent, or Firm—Herbert Dubno

[57] ABSTRACT

In order to determine the nonlinear refractive index coefficient of a material which, once inserted into a Fabry-Perot cavity (1), has an optically bistable behavior, the output power (12; 13) of the cavity (1) is measured in function of the power (1) of an amplitude-modulated optical input signal to obtain the material hysteresis loop; the hysteresis loop saturation region is detected, where the phase ($\phi$) of the electromagnetic field associated with the signal within the cavity is a linear function of the output power; the values of the phase ($\phi$) in said region are obtained from the output and input power values (12; 13; 11) and the nonlinear refractive index coefficient (n2) is obtained from the angular coefficient of the straight line representing said phase.

5 Claims, 4 Drawing Sheets

METHOD OF MEASURING THE NONLINEAR REFRACTIVE INDEX COEFFICIENT OF A BISTABLE RESONANT CAVITY OPTICAL COMPONENT

FIELD OF THE INVENTION

The present invention relates to bistable optical devices and, more particularly, to a method of determining the nonlinear refractive index coefficient in such devices.

BACKGROUND OF THE INVENTION

Bistability is a well known phenomenon, and the hysteresis of magnetic materials in order to manufacture bistable memories, has been long since exploited. The phenomenon is characterized by the existence of two values of an output quantity (corresponding to material saturation and relaxation, respectively) for the same value of an input variable, the attainment of either output value depending on the direction in which the input value is made to vary.

More recently the same phenomenon has been observed in optical devices (interferometers) made of materials with nonlinear properties, i.e. materials in which certain intrinsic parameters (such as refractive index and absorption constant) depend on the optical power inside the device. More particularly, in most of the materials of interest for optical communication, nonlinear refractive index can be expressed as the sum of a constant term and of a term depending on the power I of the signal in the device, according to relation $$n = n0 + n2 \cdot I$$

where n0 is the linear refractive index (which is constant), while n2 is the so-called nonlinear refractive index coefficient.

Present interest in optical communication systems, which allow much higher speeds than electronic systems, has led to proposals to exploit optical bistability in the implementation of digital memories or logic elements and circuits capable of replacing as far as possible the electronic components in such systems. Optical memory devices for use e.g. in optical switching and processing systems have been widely described in the literature, such devices using active or passive Fabry-Perot interferometric cavities.

For correct use of one of these devices, its characterization also from the bistability standpoint will be necessary and more particularly, the nonlinear refractive index coefficient must to be determined. Various methods are known for measuring such a coefficient in the nonlinear material from which the device is made. The simplest method is based on interferometric techniques and is described by D. Milam and M. J. Weber in a paper entitled "Measurement of nonlinear refractive index coefficient using time-resolved interferometry: Applications to optical materials for high-power neodymium lasers", Journal of Applied Physics, Vol. 47, 1976, pages 2497 and ff.

According to this method a sample of the material is introduced into an interferometer branch, a variable-intensity light beam is launched into the sample so as to cause refractive index variation, and the interference fringe shifts due to such index variations are measured to obtain n2. A correct evaluation of the positions of the visibility maxima and minima requires accurate digital processing of the experimental data to eliminate the noise present in the measurement.

However, measuring n2 directly in a device under operating conditions could be more significant, since it is to be presumed that the nonlinear refractive index coefficient of a material, like the linear refractive index, may be modified when incorporating the material into a device. The above method could theroetically be applied also to measure coefficient n2 of a device in addition to that of the material, yet such a measurement would require a more complex experimental system than used in practical applications of the devices (bistable lasers) under test.

A method of characterizing bistable semiconductor lasers has already been suggested by the Applicant (EP-A 0 343 610, published on Nov. 29, 1989), where the nonlinear refractive index coefficient is measured in the device under operating conditions, and the same equipment as used in the practical application of the device (e.g. in signal regeneration and/or amplification systems) is used for the measurement. According to that method, the laser output power is measured as a function of the input power, to determine the hysteresis loop of said the output power; the switching points between the two stable states of the laser are identified by using the power values measured; the output and input power values relevant to such points are memorized; and the value of the nonlinear refractive index coefficient of the nonlinear material which is used for manufacturing the laser is obtained from the output and input power values relevant to at least one of the points.

The method proposed has, however, some disadvantages depending on the necessity of identifying the switching points; actually, the transition regions including such points are defined not only by the optical behavior of the material, but also by the electrical characteristics of the components by which the hysteresis loop is detected; in addition these transitions are rather unstable in time, that is why repeated averages of the values obtained are to be computed. As a consequence switching point positions can be evaluated only within a certain range, and not precisely.

OBJECT OF THE INVENTION

It is object of the invention to overcome these disadvantages to provide an improved method that does not require the determination of the switching points, but that exploits the saturation and relaxation regions of the hysteresis loop, which regions, as known, are more stable. The method is also suited for determining the nonlinear coefficient both in passive and in active components and also allows determination of linear refractive index.

SUMMARY OF THE INVENTION

The invention provides a method wherein: the saturation and relaxation regions of the hysteresis loop are identified, where the phase of the electromagnetic field of the optical signal inside the cavity is a linear function of the output power; the output and input power values relevant to at least one of said regions are memorized; the phase values in said region are obtained from the memorized power values; the angular coeffcient of the straight line representative of the phase in said region is determined; and the nonlinear refractive index coefficient is obtained from said angular coefficient, from the cavity length and from the wavelength of the pump signal.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
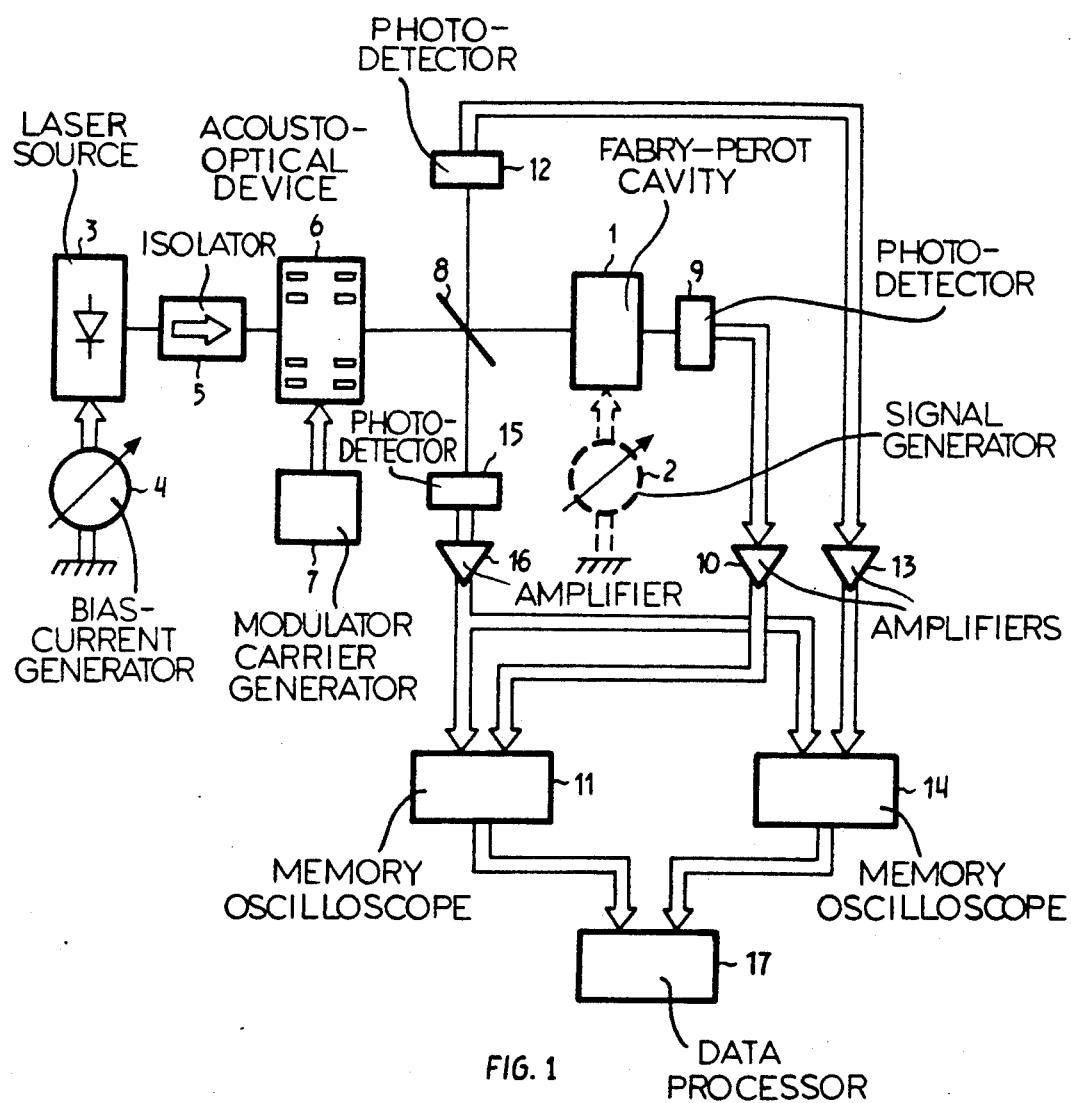
FIG. 1 is a schematic representation of the apparatus used for implementing the method.

Referring to FIG. 1, in which double lines represent electrical connections and single lines represent optical signal paths, the component 1 under test, can be a simple passive or active Fabry-Perot cavity made of a material with nonlinear optical characteristics. If the component under test is an active semiconductor component, it is connected to a generator 2 of a highly stable bias current, which causes the component (here a laser) to operate near the stimulated emission threshold, so that device 1, 2 operates as an amplifier.

Component 1 is brought to bistable operation conditions by an optical pump signal, having a wavelength slightly different from one of the cavity resonance wavelengths. More particularly, if the nonlinear material is a focusing material (coefficient n2>0), the pump signal wavelength must be slightly greater than that of the peak considered. The opposite condition applies if n2>0. The pump signal is generated by a semiconductor laser 3, connected to a respective bias current generator 4, which is also highly stable. For drawing simplicity, the systems for stabilizing the working temperatures of component 1 and laser 3 are not shown, since their function is not relevant to the invention.

In the present invention, the determination of the nonlinear refractive index coefficient of cavity 1 exploits the hysteresis loop expressed by the light intensity outgoing from the cavity as a function of the input light intensity.

The cavity output intensity will advantageously be the transmitted intensity, if the component under test is an active component, and the reflected intensity in case of a passive component; in fact in the latter case the reflectivity of the mirrors which delimit cavity 1 and/or the material absorption could excessively attenuate the transmitted signal. Yet, the hysteresis loops can be determined both in transmission and in reflection in order to completely characterize the component, utilising also the method described in the above-mentioned EP-A 0 343 610. FIG. 1 shows the apparatus in its most general form, which allows contemporaneous detection of both hysteresis loops.

For that detection, the beam generated by laser 3 is sent, via an isolator 5, to an acousto-optical device 6, driven by an amplitude-modulated carrier, more specifically a carrier modulated by a sinusoidal signal. Isolator 5 is to prevent back-reflections which could annoy the measurement. Reference 7 represents the whole of the means generating the modulated carrier. The beam outgoing from acousto-optical device 6 (e.g. a beam exhibiting first order Bragg diffraction), which has a sinusoidally varying intensity, is split by a beam splitter 8 into a transmitted partial beam and a reflected partial beam. The transmitted partial beam is applied to the component 1 under test and is partly reflected from the input face and partly transmitted, after being possibly optically amplified by component 1, if this is an active component.

The partial beam transmitted by component 1 is collected by a photodetector 9, whose output is connected through an amplifier 10 to input y of a memory oscilloscope 11 operated in x-y mode. The partial beam reflected by component 1 is collected by mirror 8 and sent to a photodetector 12 whose output is connected through an amplifier 13 to input y of a second memory oscilloscope 14, this also operated in x-y mode.

The partial beam reflected by beam splitter 8 is collected by a further photodetector 15 whose output is connected through an amplifier 16 to input x of oscilloscopes 11, 14. For the sake of simplicity, the various optical systems which collimate and focus the light beams have not been shown as they form no part of the present invention.

Oscilloscope 11 stores the amplitude of the signal from photodetector 9 (which is proportional to intensity I2 of the beam transmitted by component 1) in function of the amplitude of the signal from photodetector 15 (which is proportional to intensity I1 of the beam launched into the component). Similarly, oscilloscope 14 stores the amplitude of the signal from photodetector 12 (which is proportional to intensity I3 of the beam reflected by component 1) in function of intensity I1. The hysteresis loops of component 1 are thus built up. A data processing unit 17, which is connected to oscilloscopes 11 and 14, identifies the saturation and relaxation regions of the hysteresis loops, obtains transmittivity and/or reflectivity values in such regions, and calculates the nonlinear refractive index coefficient and the linear refractive index by using said values as well as those of the amplification or attenuation factor, of the finesse parameter (which depends on Fabry-Perot cavity mirror reflectivity) and of the interferometric cavity length, separately determined or known a priori and stored inside it.

Clearly, if only one of the two hysteresis loops is used or if the two hysteresis loops are determined in different instants, a single memory oscilloscope which receives at input y the signals outgoing from detector 9 or from detector 12 will be sufficient.

Figure 2:
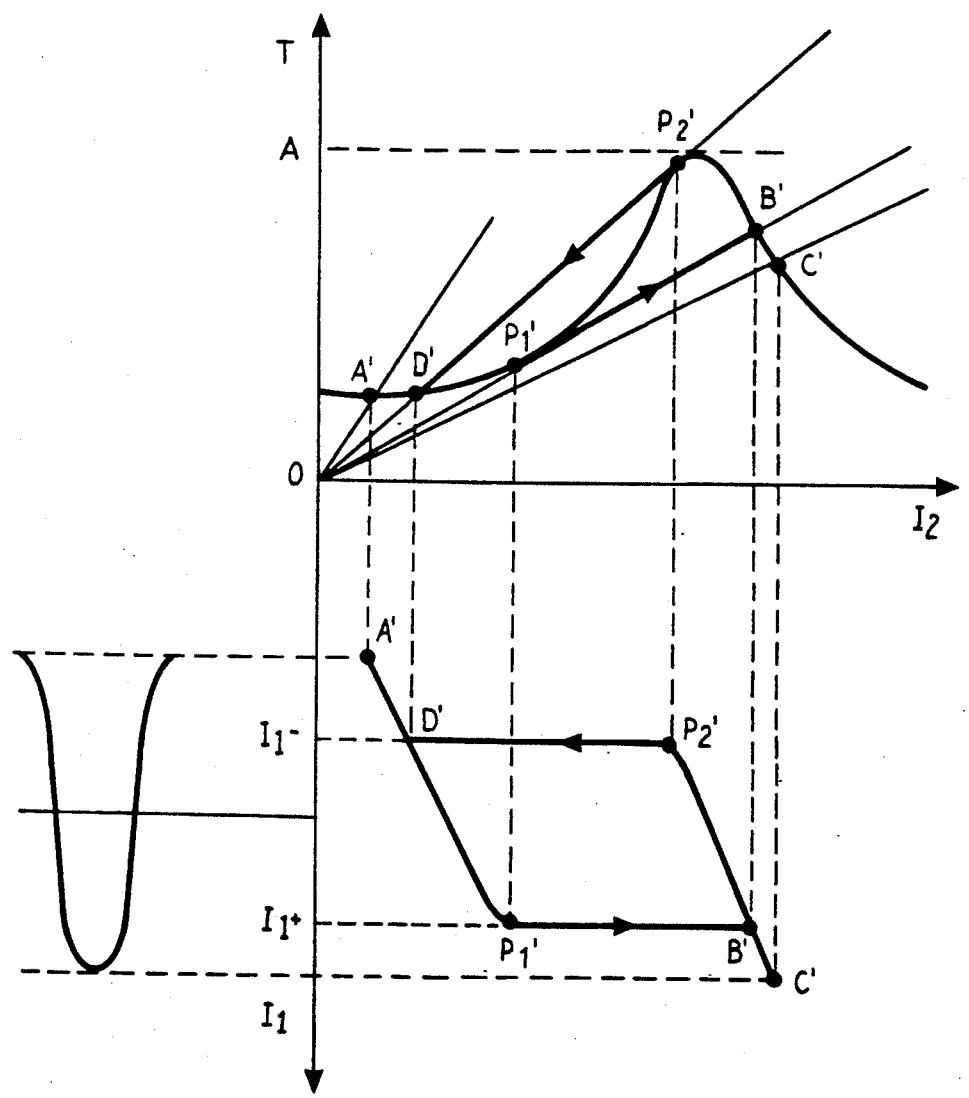
FIG. 2 shows the component transmittivity versus the intensity of the component output beam and the hysteresis loop in transmission.
Figure 3:
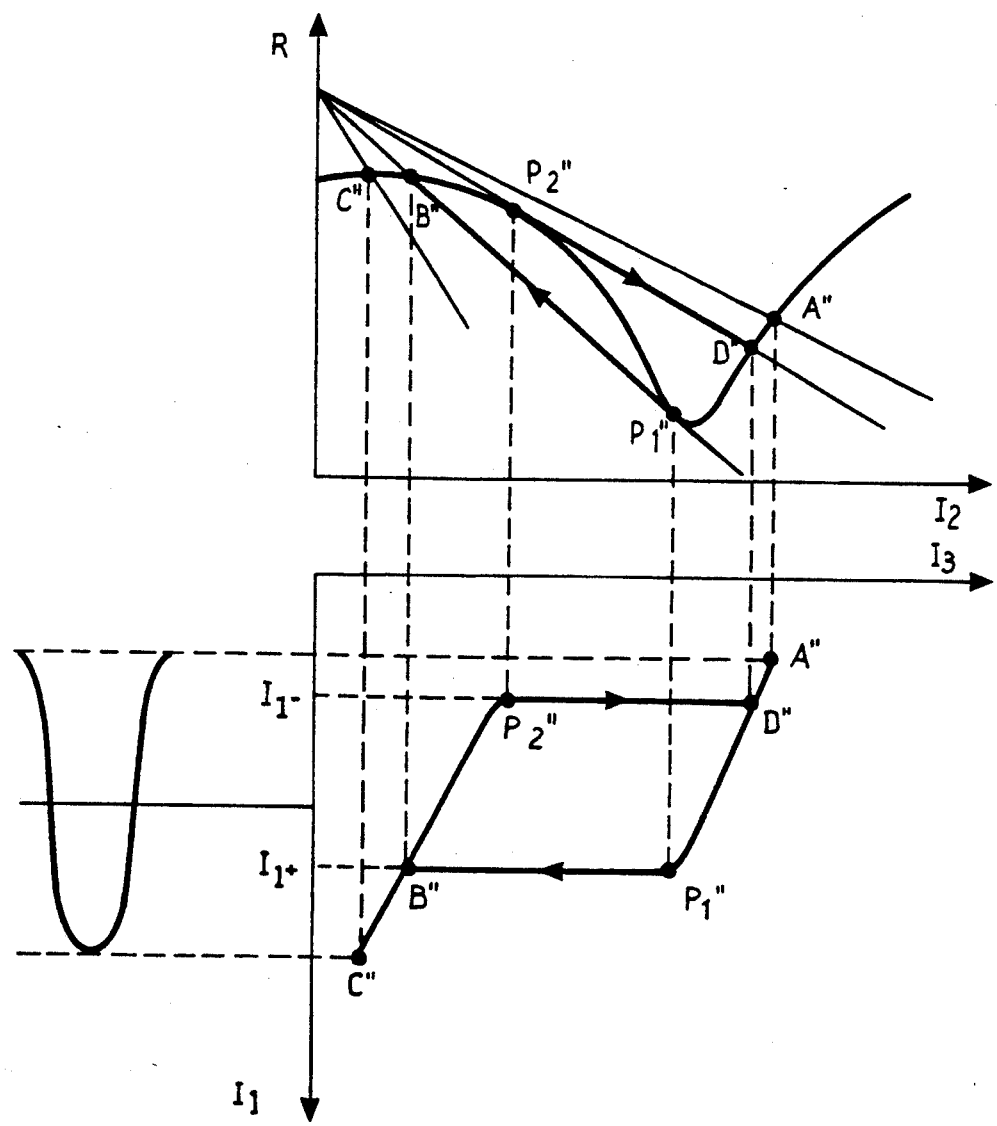
FIG. 3 shows the component reflectivity versus the intensity of the component output beam and the hysteresis loop in reflection.
Figure 4:
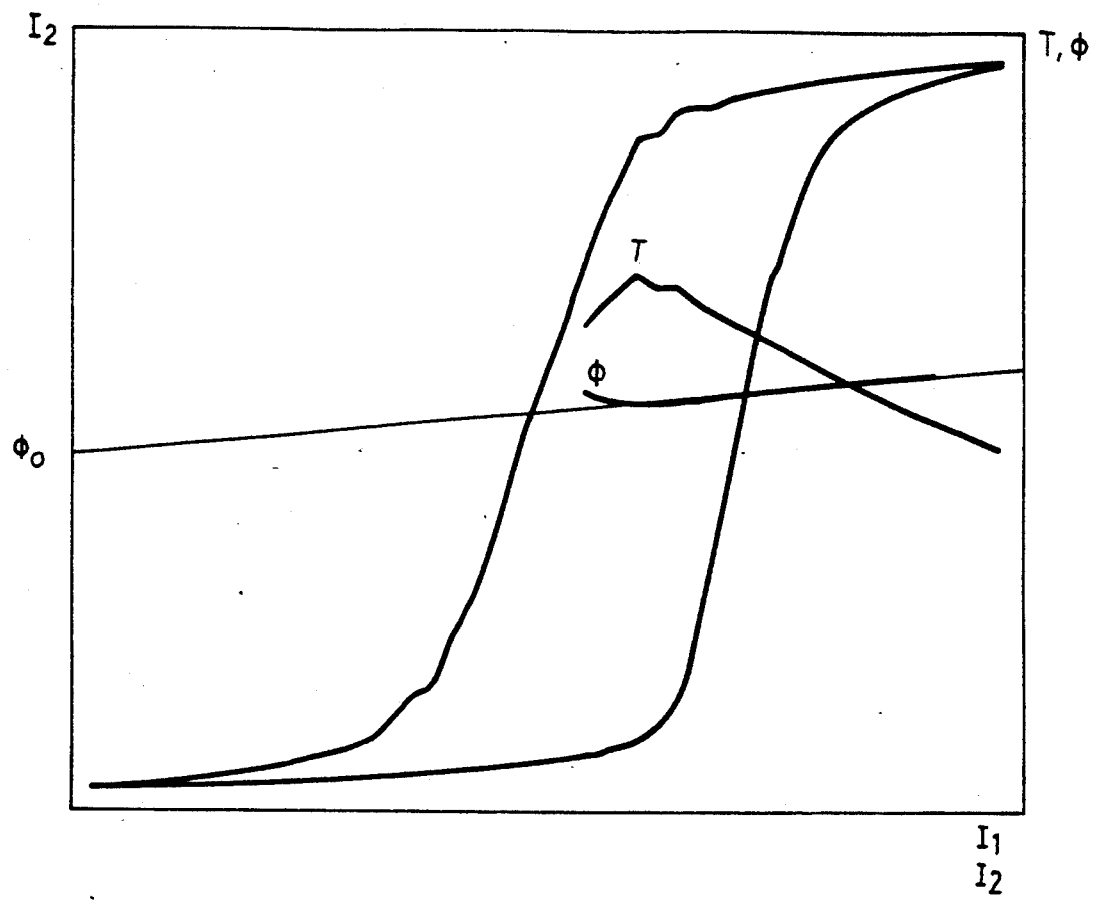
FIG. 4 is a diagram of the phase versus the transmitted power.

The theoretical principles on which the method of the invention is based will now be disclosed in more detail, with reference also to the diagrams of FIGS. 2 to 4.

FIG. 2 shows transmittivity T versus I2 and the hysteresis loop of I2 versus I1. The straight lines represent T when T is expressed by the ratio I2/I1; the curve represents the function $$T = \frac{A}{1 + AF\sin^2\phi} \quad (1)$$

which links T to the parameters of a nonlinear Fabry-Perot cavity filled with a material having refractive index $n = n0 + n2 \cdot I2$, $\phi$ being the phase of the electromagnetic field inside the cavity, given by:

$$\phi = (2\pi/\lambda 1) \cdot n0 \cdot L + (2\pi/\lambda 1) \cdot n2 \cdot L \cdot I2 \quad (2)$$

Relations (1), (2) are valid for small optical signal approximation (i.e. at levels far from saturation of the nonlinear effect, which takes place with different mechanisms and thresholds according to the type of material and according to whether the device is active or passive) and assuming for simplicity plane wave propagation. In the relations above, I2, I1, n0, n2 have the meaning already discussed; λ1 is the wavelength of laser 3. A is the transmission factor of component 1 under resonance conditions; F is the finesse parameter of the cavity. Only the first peak (the closest one to I2=0) of the curve which represents relation (1) has been considered. The operating condition in which this peak can be exploited is easily obtained by a suitable choice of the wavelength difference between component 1 and laser 3, more particularly by using the resonance wavelength of component 1 closest to λ1.

FIG. 3 shows reflectivity R versus I2 and the hysteresis loop of I3 versus I1. Straight lines represent R when R is expressed by the ratio I3/I1; the curve represents the function $$R = 1 + BT = 1 + \frac{BA}{1 + AF\sin^2\phi} \quad (3)$$

which links R to the Fabry-Perot cavity parameters; in such relation, A, F and $\phi$ have the meaning above and $B = (rG^2 - 1)/G \cdot (1-r)$ is the efficiency factor of the reflection hysteresis loop, G being the single-pass gain of the cavity and r the reflectivity of the mirrors of the same cavity. Relation (3) is valid under the same conditions as relation (2).

Corresponding points are indicated with a prime in FIG. 2 and with a double prime in FIG. 3.

The measurement in transmission will be first considered. Straight lines T=I2/I1 have angular coefficients 1/I1 varying with the device input signal. Considering for sake of simplicity the portion of input signal comprised between two consecutive minima of the amplitude modulation, for a given value of I1 the corresponding straight line T=I2/I1 intersects the curve at one or more points which may be stability or instability points. More particularly, when I1 is minimum (maximum angular coefficient), the intersection point is unique (point A'); as I1 increases, the angular coefficient decreases and, according to the value thereof, the straight line can intersect the curve not only within the segment adjacent to point A' but also in proximity of the maximum of the curve itself. For a certain value I1+ of I1 the straight line becomes tangent to the curve at P1' and has an intersection point at B': the points between A' and P1' are stable points, while possible further intersections points are unstable points, as well known to the skilled in the art. A further increase in I1, and hence a further decrease in the angular coefficient of the straight line, causes switching from P1' to B' (so that P1' represents the first switching point) and then the intersection point moves along the decreasing curve segment starting in B', till it reaches point C' in correspondence with the maximum of I1. Also the points between B' and C' are stable points. Segment B'-C' belongs to the so-called saturation region. Now I1 decreases and the intersection points between the straight line and the curve lie within segment C'-P2', which defines the saturation region. At point P2' (corresponding to value I1⁻ of I1) the situation is analogous to that at P1': the straight line is tangent to the curve and in addition there is an intersection at point D', so that the further decrease of I1 causes switching and the straight line moves along segment D'-A', thus closing the loop. Segment A'-P1' forms a relaxation region, of similar characteristics to the saturation region. The hysteresis loop is then defined by trajectory A'-P1'-B'-C'-P2'-D'-A'.

The value of n2 can be obtained from the values of I2 and I1 in segments A'-P1' and C'-P2'. In fact in such segments the following relation will obviously be valid:

$$\arcsin\sqrt{(1/F)\cdot(T^{-1}-1/A)} = (2\pi/\lambda 1)\cdot n0\cdot L + (2\pi/\lambda 1)\cdot n2\cdot L\cdot I2 \quad (4)$$

where the first member expresses the value of $\phi$ in function of T obtained by solving relation (1) with respect to $\phi$, while the second member discloses the linear behavior of $\phi(I2)$ according to equation (2). So, the function at the first member of relation (4) will be represented by a straight line with angular coefficient proportional to n2.

Thus, to implement the method of the invention, the various pairs of values (I2, I1) defining the hysteresis loop of the output power will be determined by means of memory oscilloscope 11 (FIG. 1), and the pairs relevant to segment C'-P2' (or A'-P1') will be stored; λ1, L, F, A are known or can be independently determined (by a spectral measurement on laser 3, by a measurement of the spectral distribution of the Fabry-Perot cavity, and by the method described in EP-A-0 343 610, respectively). Processing unit 17 can hence build up the straight line which approximates the function at the first member of relation (4) in the segments considered and obtain the angular coefficient of such a straight line, which coefficient, once divided by 2πL/λ1, gives n2. The values of phase $\phi$ obtained from the values of I2, I1 measured by means of the equipment and relevant to the saturation region (I2~Imax) are plotted versus I2 in the graph of FIG. 4, where for clarity also the hysteresis loop of I2 versus I1 is plotted. The linear phase behaviour is clearly shown.

By extrapolating the data from which the straight line has been built up, processing unit 17 can also determine value $\phi$0 of fase $\phi$ corresponding to I2=0; taking into account relation (2), such value is $(2\pi/\lambda 1)\cdot n0\cdot L$, and the linear refractive index n0 can immediately be obtained therefrom.

The operation is completely analogous if reflectivity is taken into consideration instead of transmittivity, as it will be convenient in case of a passive component. By obtaining $\phi$ from relation (3) and taking into account that I3=I1+BI2 the following relation will be obtained:

$$\arcsin\sqrt{(1/F)\cdot[B/(R-1)-1/A]} = (2\pi/\lambda 1)\cdot n0\cdot L + (2\pi/\lambda 1\cdot B)\cdot n2\cdot L\cdot(I3-I1) \quad (5)$$

and the angular coefficient of the straight line which approximates the first member of (5) will be obtained as before, by using the values of I3 and I1. The phase and hysteresis loop graphs obtained from the reflectivity are basically identically with those shown in FIG. 4.

Of course it is sufficient to store the values of I2 (or I3) and I1 relevant to either the saturation or the relaxation region; advantageously, the saturation region will be taken into consideration, where the values of I2 or I3 are higher, since this reduces the influence of systematic deviations in evaluating the origin of the hysteresis loop. For that reason, FIG. 4 shows phase $\phi$ in the saturation region.

In addition, by determining, as described in EP-A-0 343 610, the angular coefficients of the straight lines which approximate the transition regions in the transmission and reflection hysteresis loops, the values of F, G, A in addition to the values of n2 will be obtained and the component will be completely characterized.

We claim:

1. A method of measuring a nonlinear refractive index coefficient of a resonant cavity manufactured from a material with nonlinear optical characteristics and brought to bistable operating conditions by an optical pump signal of varying intensity wherein an output power of the cavity is measured as a function of an input power to determine the hysteresis loop of said output power, said method comprising the steps of:

identifying saturation and relaxation regions of said hysteresis loop where a phase of an electromagnetic field of the optical signal inside the cavity is a linear function of the output power;

storing values of the output and input power relevant to at least one of said regions;

computing phase values in said at least one region from the stored values of output and input power; and determining an angular coefficient of a straight line representative of the phase in said at least one region, and obtaining a nonlinear refractive index coefficient from said angular coefficient from a length of the cavity and from a wavelength of the pump signal.

2. A method as claimed in claim 1 wherein said cavity is an active cavity, said output power is a transmitted power, and values of the phase are derived from a component transmittivity expressed as a ratio between transmitted power and input power of said cavity.

3. A method as claimed in claim 1 wherein said cavity is a passive cavity, said output power is a reflected power, values of the phase are derived from component reflectivity expressed as a ratio between a reflected power and an input power, and the nonlinear refractive index coefficient is obtained from said angular coefficient, from a length of the cavity, from the wavelength of the pump signal and from an efficiency factor of the hysteresis loop of the reflection, said factor being given by $B = (rG^2 - 1)/G.(1 - r)$, where G is a single-pass gain of the cavity and r a reflectivity of the mirrors of the same cavity.

4. A method as claimed in claim 1 wherein, the values of the output power and input power relevant to the saturation region are stored.

5. A method as claim in claim 1 wherein angular coefficients of straight lines which approximate transition regions of hysteresis loops for transmission and reflection are determined from the input and output powers, and a transmission factor, a finesse parameter and a single-pass gain of the cavity are derived from said angular coefficients.

* * * * *